United States Patent [19]

Fukuma et al.

[11] Patent Number: 4,859,051
[45] Date of Patent: Aug. 22, 1989

[54] EYE TESTING APPARATUS

[75] Inventors: Yasufumi Fukuma; Ikuo Kitao; Yasuo Kato, all of Tokyo, Japan

[73] Assignee: Tokyo Kogaku Kikai Kabushiki Kaisha, Tokyo, Japan

[21] Appl. No.: 137,718

[22] Filed: Dec. 24, 1987

[30] Foreign Application Priority Data

Dec. 25, 1986 [JP] Japan ................. 61-310009

[51] Int. Cl.$^4$ .............................................. A61B 3/10
[52] U.S. Cl. .................................... 351/211; 351/212
[58] Field of Search ............... 351/211, 212, 247, 205, 351/208

[56] References Cited

FOREIGN PATENT DOCUMENTS 29446  2/1983  Japan .................................. 351/212

Primary Examiner—Rodney B. Bovernick
Attorney, Agent, or Firm—Finnegan, Henderson, Farabow, Garrett & Dunner

[57] ABSTRACT

An eye testing apparatus, in which a cornea reflecting image and a retina reflecting image formed by projecting each target mark image onto a cornea and a retina of an eye to be tested are projected to a slight receiving portion through a measuring optical system, and in which a corneal configuration and a refractive power of the eye to be tested are measured according to a signal detected by the light receiving portion, characterized in that the light receiving portion includes a two-dimensional light receiving element, the measuring optical system simultaneously projecting the cornea reflecting image and the retina reflecting image to different areas of the two-dimensional light receiving element.

17 Claims, 7 Drawing Sheets

1

EYE TESTING APPARATUS

BACKGROUND OF THE INVENTION

1. Field of the Invention

This invention relates to an eye testing apparatus for measuring a corneal configuration, an eye refractive power, etc. of an eye to be tested.

2. Description of the Related Art

Heretofore, there has been known an eye testing apparatus for measuring a corneal configuration, an eye refractive power, etc. of an eye to be tested, in which a cornea reflecting image and a retina reflecting image formed by projecting a target mark image to the cornea and retina of an eye to be tested are projected to respective light receiving portions capable of photoelectric transfer through a measuring optical system and in which the corneal configuration and eye refractive power of the eye to be tested are arithmetically measured according to a detecting signal of the respective light receiving portions.

In this conventional eye testing apparatus, a light receiving portion for measuring the corneal configuration and a light receiving portion for measuring the eye refractive power are separately provided. Therefore, an optical path switching mechanism, a light receiving portion driving circuit, an arithmetic processing system, etc. must be separately provided. Thus, the conventional eye testing apparatus has the inconvenience in that the number of parts required are large and, therefore, the whole eye testing apparatus can not be made small. Further, in the conventional eye testing apparatus, since it is required to obtain data for corneal measurement and data for eye refractive power by scanning the respective light receiving portions separately, it takes long time for measurement.

SUMMARY OF THE INVENTION

The present invention was accomplished in view of the above-mentioned problems. It is therefore a first object of the present invention to provide an eye testing apparatus, in which a two-dimensional light receiving element is used in a light receiving portion where a corneal reflecting image and a retina reflecting image of an eye to be tested are projected, and a measuring optical system is designed as such that the corneal reflecting image and retina reflecting image are simultaneously projected to different areas of the two-dimensional light receiving element, so that the number of parts required for the whole eye testing apparatus is reduced compared with the conventional apparatus and the whole apparatus is made much smaller, and the time required for measurement is shortened in view of the whole apparatus.

A second object of the present invention is to provide an eye testing apparatus, in which a two-dimensional light receiving element is used in a light receiving portion where a corneal reflecting image and a retina reflecting image of an eye to be tested are projected, and a measuring optical system is designed as such that the corneal reflecting image and retina reflecting image are simultaneously projected to different areas of the two-dimensional light receiving element, and an annular pattern for measuring the refrative power can be moved in order to avoid that the corneal reflecting image and retina reflecting image are formed in adjacent relation on the two-dimensional light receiving element based on a severe myopia of the eye to be tested.

DETAILED DESCRIPTION OF THE PREFERRED EMBODIMENTS

I-A. Optical Arrangement of the Whole Apparatus

Figure 1:
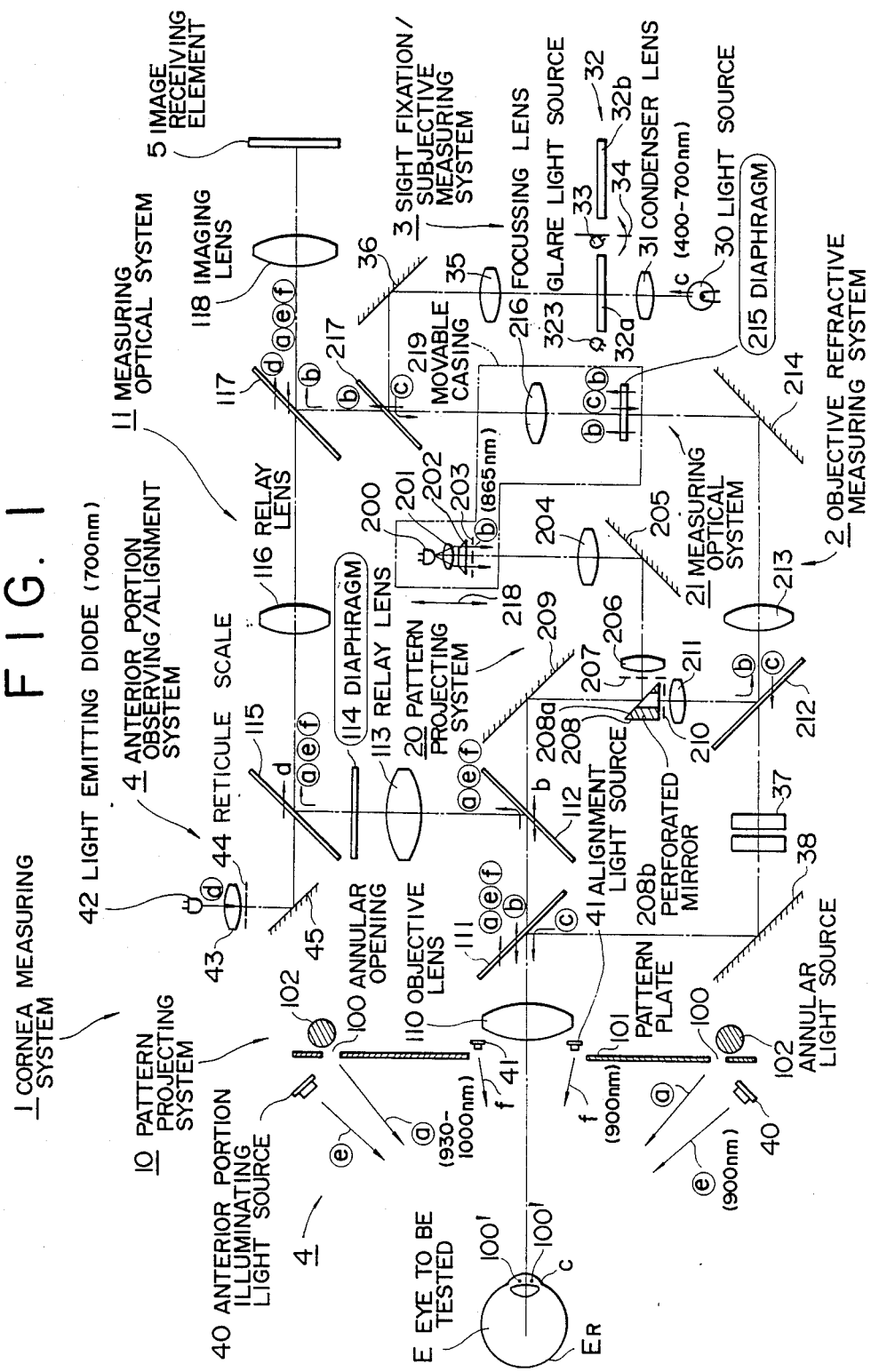
FIG. 1 is an optical arrangement of a whole eye testing apparatus according to the present invention.

FIG. 1 shows an optical arrangement of a whole eye testing apparatus according to the present invention. This eye testing apparatus generally comprises a cornea measuring system 1 for measuring a radius of curvature of a cornea C of an eye E to be tested, an objective refractive power measuring apparatus 2 for objectively measuring the refractive power of the eye E, a sight fixation/subjective measuring system 3 for projecting a sight fixation mark for fixing a sight of the eye E in order to fix a sight axis of the eye E during a measurement and a sight mark for a subjective test, and an anterior portion observing/alignment system 4 for observing an anterior portion of the eye E and aligning an optical axis of the apparatus and the sight axis of the eye E. An optical axis of the anterior portion observing/alignment system 4 is partly common with that of the cornea measuring system 1.

I-B. Cornea Measuring System 1

The cornea measuring system 1 is largely divided into a pattern projecting system 10 for projecting an annular pattern for measuring the radius of curvature of the cornea C towards the cornea C, and a measuring optical system 11 for measuring the size and configuration of a cornea reflecting image of the annular pattern.

The pattern projecting system 10 comprises a pattern plate 101 having an annular opening 100, and an annular light source 102 disposed behind the opening 100 and for emitting a cornea measuring light (hereinafter, this cornea measuring light is denoted by reference character a ) having a wavelength of from 930 nm to 1000 nm. Light emitted by the light source 102 passes through the opening 100 and is projected, as a projecting light, onto the cornea C of the eye E. The projecting light is reflected by the cornea C and forms a virtual image 100' of the opening 100. The cornea measuring light a reflected by the cornea C enters into a measuring optical system 11 as if it were emitted by the virtual image 100'.

The measuring optical system 11 comprises an objective lens 110, a half mirror 111 for reflecting a visible light having a wavelength of from 400 nm to 700 nm (hereinafter, this visible light is denoted by reference character c and allowing light in a long wavelength area of 800 nm or more including the cornea measuring light a (wavelength of from 930 nm to 1000 nm) to pass therethrough, a half mirror 112 for allowing an infrared light having a wavelength of 865 mn (hereinafter, this infrared light is denoted by reference character b to pass therethrough and reflecting an infrared light having a wavelength of 900 nm or more, a relay lens 113, a diaphragm 114, a half mirror 115 for allowing a red light having a wavelength of 700 nm (hereinafter, this red light is denoted by reference character d ) to pass therethrough and reflecting the cornea measuring light a , a relay lens 116, a half mirror 117 for reflecting the infrared light b and allowing the cornea measuring light a and the red light d to pass therethrough, an imaging lens 118, and an area CCD 5 as an image receiving element.

Figure 3:
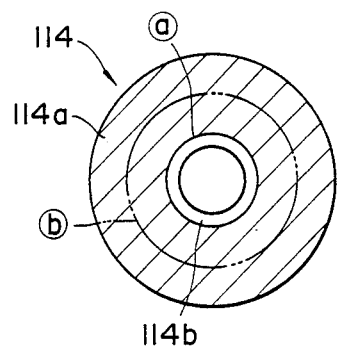
FIG. 3 is a plan view of a diaphragm 114.

Herein, the diaphragm 114, as shown in FIG. 3, is divided into two portions of a peripheral portion 114a and a central portion 114b. The peripheral portion 114a cuts light having a wavelength of 930 nm or more, whereas the central portion 114b allows light having a wavelength of 900 nm or more to pass therethrough. That is, light having a wavelength of 900 nm or more but of 930 nm or less (hereinafter, this light is denoted by reference character e ) is allowed to pass through any area of the diaphragm 114. The cornea measuring light a reflected by the cornea C is condensed by the objective lens 110 and then, allowed to pass through the half mirror 111. And, the cornea measuring light a is reflected by the half mirror 112 and is allowed to pass through the central portion 114b of the diaphragm 114 through the relay lens 113. Thereafter, the cornea measuring light a is reflected by the half mirror 115, then guided to the half mirror 117 by the relay lens 116, and then allowed to pass through the half mirror 117. The cornea measuring light a is imaged, as a cornea measuring ring pattern 100" (see FIGS. 6 and 7), on the light receiving element 5 by the imaging lens 118.

Even if the anterior portion (iris) of the eye E is illuminated during the formation of the virtual image 100' of the opening 100 by projecting the cornea measuring light a , the reflecting light does not reach the image receiving element 5 because it is cut by the peripheral portion 114a of the diaphragm 114, and therefore, only the cornea pattern 100" is projected onto the image receiving element 5.

I-C. Objective Refractive Power Measuring System 2

C-1: Pattern Projecting System 20

Figure 2:
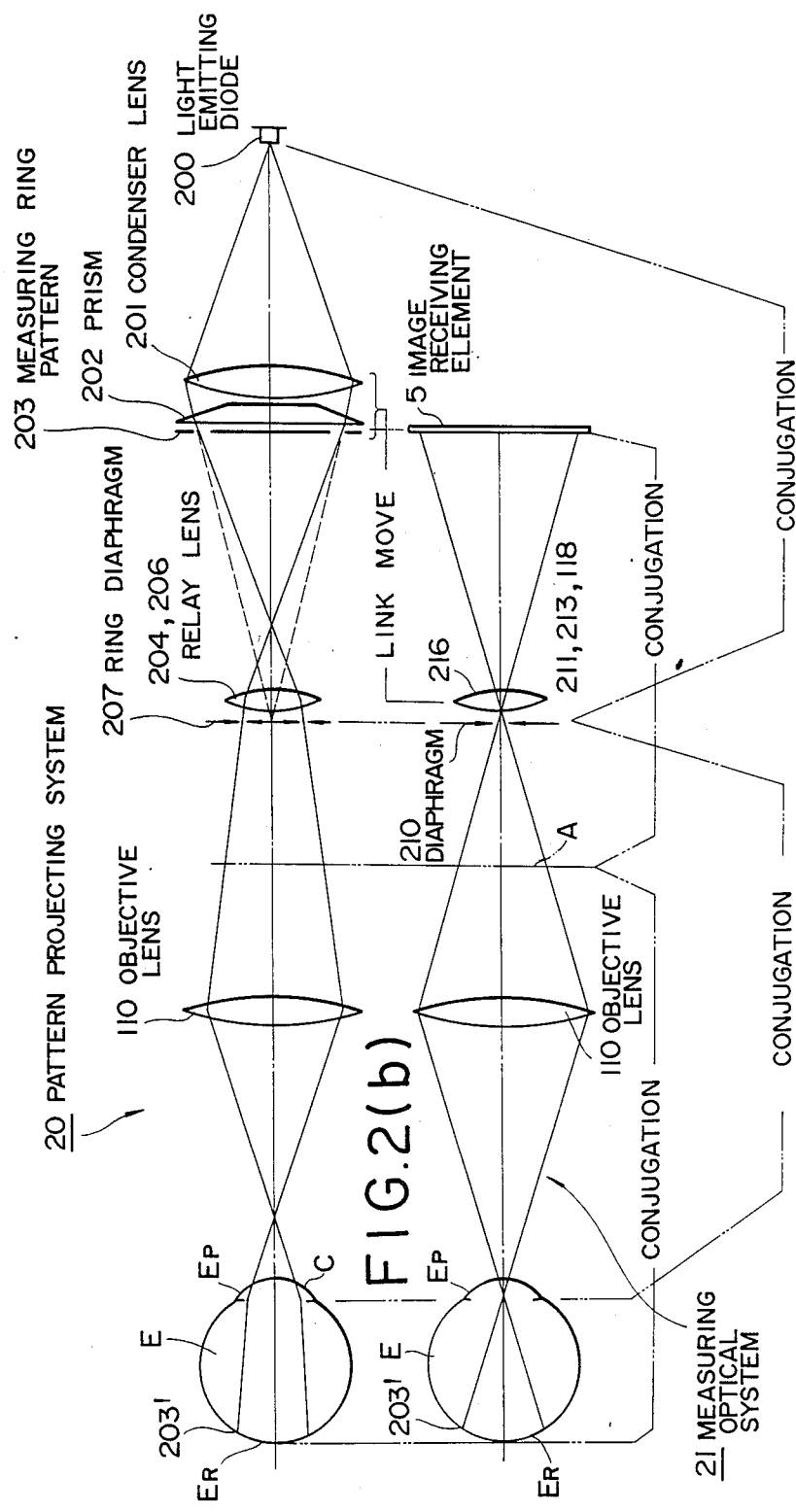
FIG. 2 is a schematic view of an optical path of an objective refractive power measuring system.

The objective refractive power measuring system 2, as shown in FIG. 1, includes a pattern projecting system 20. FIG. 2(a) is a schematic view of an optical path of the pattern projecting system 20 of FIG. 1. A refractive power measuring light having a wavelength of 865 nm (hereinafter, the above-mentioned infrared light b is referred to as the "refractive power measuring light b ") emitted by a light emitting diode 200 is condensed by a condenser lens 201, then refracted by the conical prism 202, and then projected to a ring pattern 203 for measuring the refractive power. The refractive power measuring light b which has passed through the ring pattern 203, is projected to a ring diaphragm 207 through a relay lens 204, a mirror 205 (see FIG. 1) and a relay lens 206. After passing through the ring diaphragm 207, the refractive power measuring light b is reflected by a reflecting surface 208a of a perforated mirror 208. And, thereafter, the refractive power measuring light b is reflected by a mirror 209, then allowed to pass half mirrors 112 and 111 as a component element of the measuring optical system 11 of the cornea measuring system 1, and then projected, as an image 203' (see FIG. 2) of the ring pattern 203, onto a retina $E_R$ of the eye E by an objective lens 110. Herein, the light emitting diode 200 and ring diaphragm 207 are optically conjugated with respect to each other, and the ring diaphragm 207 and a pupil of the eye E are in optically conjugated relation.

C-2: Measuring Optical System 21

Figure 4:
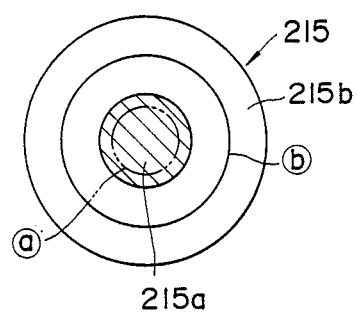
FIG. 4 is a plan view of a diaphragm 215.

FIG. 2(b) is a schematic view of an optical path of the measuring optical system 21 of FIG. 1. Light of a ring pattern 203' reflected by the retina $E_R$ of the eye E is condensed by the objective lens 110. And, after passing through the half mirrors 111 and 112, the light is reflected by the mirror 209 and allowed to pass through the diaphragm 10 via an opening portion 208b. After passing through a relay lens 211 via the diaphragm 210, the refractive power measuring light b is reflected by a half mirror 212 capable of passing a visible light c and then, projected to a diaphragm 215 through a relay lens 213 and a mirror 214. The diaphragm 215, as shown in FIG. 4, has a peripheral portion 215b for allowing the refractive power measuring light b of a wavelength of 865 nm to pass therethrough, and a central portion 215a for cutting the refractive power measuring light b .

The diaphragm 215 has such a characteristic, in its entire area, as not to allow the cornea measuring light a having a wavelength of from 930 nm to 1000 nm to pass therethrough but to allow the visible light c having a wavelength of from 400 nm to 700 nm to pass therethrough. By this, the refractive power measuring light b is allowed to pass only through the peripheral portion 215b of the diaphragm 215. After passing through a half mirror 217 which reflects the visible light c and allows the refractive power measuring light b to pass therethrough through a focussing lens 216, the refractive power measuring light b is reflected by a half mirror 117 of the measuring optical system 11 and is imaged, as a ring pattern image 203" (see FIGS. 6 and 7), on the image receiving element 5 by the imaging lens 118.

The focussing lens 216 and diaphragm 215 are contained within a movable casing 219 integral with the light emitting diode 200, condenser lens 201, conical prism 202, and ring pattern 203 of the pattern projecting system 20 and are movable in the direction of the optical axis as shown by an arrow 218 of FIG. 1.

In the above-described measuring optical system 21, the diaphragm 210 is optically conjugated with the position of the pupil EP of the eye E with respect to the objective lens 110, whereas the light receiving element 5 is optically conjugated with an intermediate imaging surface A (see FIG. 2) of the ring pattern 203 when the eye E has a normal vision (refractive power 0 Dioptor).

I-D. Fixation Sight and Subjective Measuring System 3

The visible light c having a wavelength of from 400 nm to 700 nm emitted by the light source 30, is condensed by the condenser lens 31 and illuminates the chart plate 32.

Figure 10:
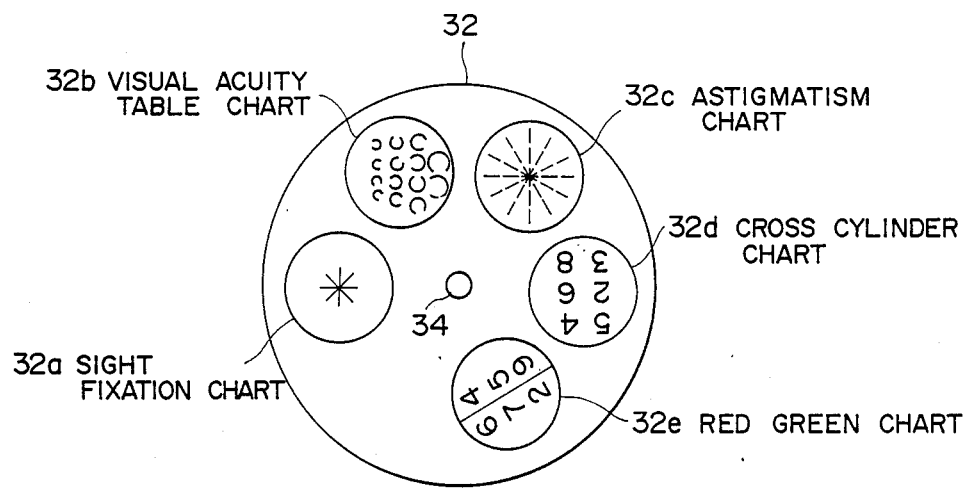
FIG. 10 is an illustration showing an example of a chart for a subjective measurement.

The chart plate 32, as shown in FIG. 10 for example, is provided on the circumference thereof with a sun burst chart (sight fixation chart) 32a as a sight fixation mark, a visual acuity table chart 32b for a subjective testing, an astigmatism chart 32c, a cross cylinder chart 32d, and a red green chart 32e. When the chart plate 32 is rotated about the shaft 34, the respective charts are selectively entered into the optical path.

An image of each chart 32a through 32e is projected to the eye E by the projecting lens 35. After reflected by the mirror 36, the image of each chart 32a through 32e is reflected by the half mirror 217, then flowed into the measuring optical system 21 of the objective refractive power measuring system 2, then passed through the diaphragm 216, then guided to the half mirror 212 through the mirror 214 and relay lens 213, then passed through the half mirror 212, and then guided to a variable cross cylinder 37. The visible light c is passed through the variable cross cylinder 37, then reflected by the half mirror 111 through a mirror 38, and then projected to the eye E by the objective lens 110. As a result, the charts 32a through 32e are observed by the eye E.

Further, a plurality of glare light sources 33 for emitting a visible light for a glare test, are disposed around the outer periphery of an inserting position of the charts 32a through 32e inserted into the optical path in the vicinity of the chart plate 32. The light sources 33 for the glare test may be disposed in the vicinity of the objective lens 110. Furthermore, in order to perform the glare test, instead of providing the light sources 33, the contrast between a vision table of the visual acuity table chart 32b and a base thereof may be changed.

I-E. Anterior Portion Observing/Alignment System

A plurality of light emitting diodes 40 for illuminating the anterior portion are disposed outside the pattern plate 101 of the pattern projecting system 10 of the cornea measuring system 1, and an infrared light having a wavelength of 900 nm (hereinafter, this infrared light is denoted by reference character e) emitted by each light emitting diode 40, illustrates the anterior portion of the eye E. The infrared light (anterior portion illuminating light) e reflected by the anterior portion is condensed by the objective lens 110, then passed through the half mirror 111, then propagated along the measuring optical system 11 of the cornea measuring system 1, and then imaged on the image receiving element 5 by the imaging lens 118.

A plurality of light emitting diodes 41 for emitting the infrared light having a wavelength of 900 nm are disposed in the vicinity of the outer periphery of the objective lens 110. The plurality of light emitting diodes 41 are served as a light source for alignment. An alignment light (hereinafter, this alignment light is denoted by reference character f) emitted by the alignment light source 41 is reflected by the eye E, then condensed by the objective lens 110, then passed through the half mirror 111 like the anterior portion illuminating light e, then propagated along the measuring optical system 11 of the cornea measuring system 1, and then imaged on the image receiving element 5 by the imaging lens 118.

In front of the half mirror 115 of the measuring optical system 11 of the cornea measuring system 1, a reticule scale projecting optical system is disposed. This reticule scale projecting system comprises a light emitting diode 42 for emitting the infrared light (corresponding to the light d, and hereinafter, this infrared light is referred to as the "scale light") having a wave length of 700 nm, a condensing lens 43 for condensing the scale light d from the light emitting diode 42, and a mirror 45 for reflecting the scale light d passed through the reticule scale 44 to flow into the measuring optical system 11.

After passing through the half mirror 115, the scale light d coming from the reticule scale 44 is imaged on the image receiving element 5 by the imaging lens 118 through the measuring optical system 11.

II. Electric Circuitry

Figure 5A:
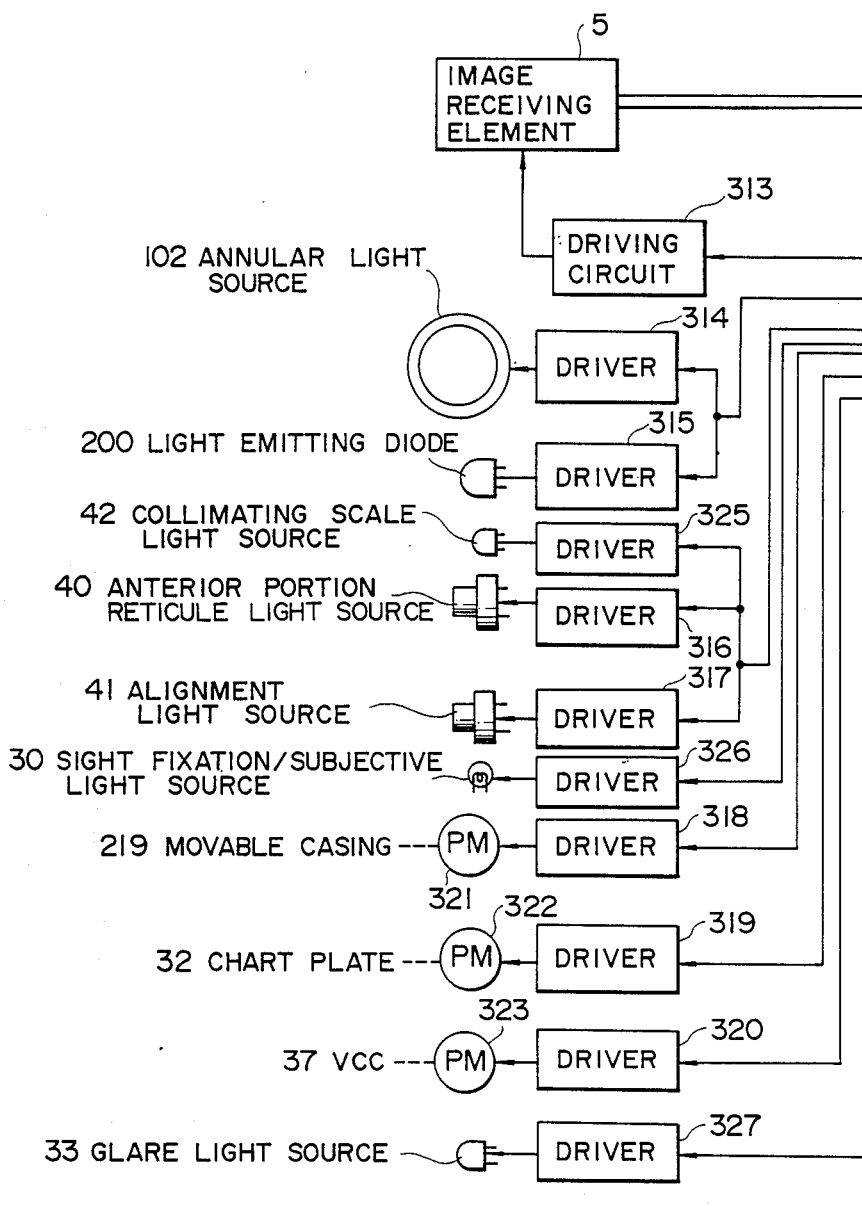
FIG. 5 is a block diagram of an electric circuit.
Figure 5B:
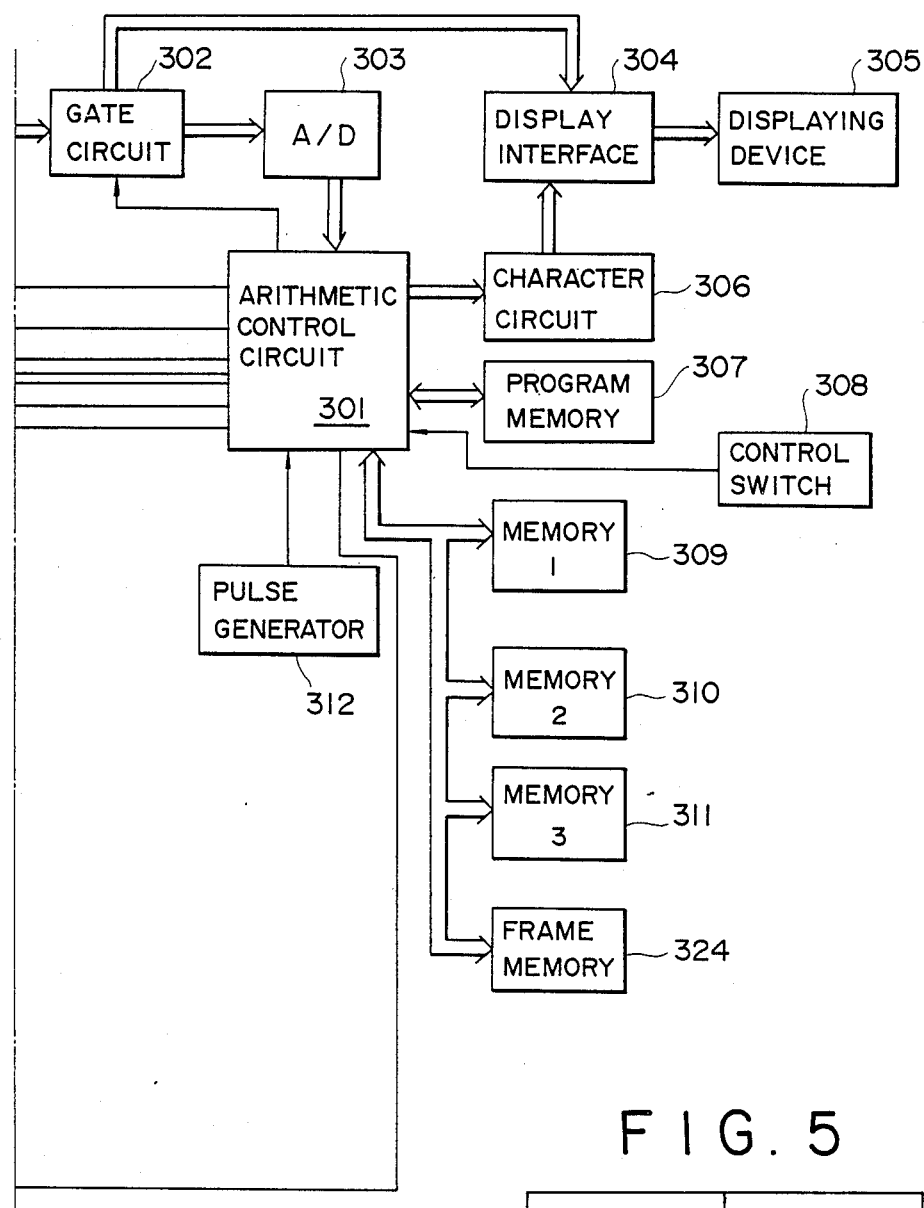
Figure 5:
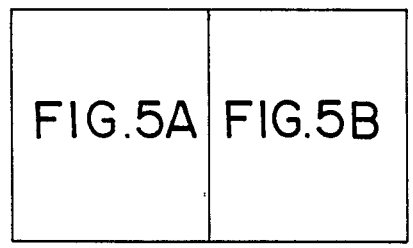

FIG. 5 is a block circuit diagram of an eye testing apparatus according to the present invention. Upon receipt of a command from an arithmetic/control circuit 301, a driving circuit 313 scans an area CCD as the image receiving element 5 and outputs the received image as an analog signal.

The arithmetic/control circuit 301 controls a gate circuit 302, and the gate circuit 302 outputs an analog signal from the image receiving element 5 towards an A/D converter 303 or a display interface 304. Upon receipt of the analog signal from the image receiving element 5 through the gate circuit 302, the display interface 304 displays the received image of the image receiving element 5 on a displaying device 305 comprising, for example, a CRT, a liquid crystal TV, or a plasma display.

The A/D converter 303 has such a function as to convert the analog signal coming from the image receiving element 5 to a digital signal, and the digital signal is input into the arithmetic/control circuit 301.

The arithmetic/control circuit 301 is connected with a frame memory 324 for memorizing data for one screen portion or a plurality of screen portions of the image received element converted into the digital signal by the A/D converter 303. Further, the arithmetic/control circuit 301 has such a function as to selectively feed a pulse from a pulse generator 312 to driver circuits 318, 319 and 320, and to count the pulse number and output it to a first memory 309 as a signal. The first memory 309 memorizes the counted value.

The driver circuit 318 feeds a pulse from the arithmetic/control circuit 301 to a pulse motor 321 for driving a movable casing 219 of the refractive power measuring system 2 and drives the pulse motor 321. The driver circuit 319 feeds a pulse to a pulse motor 322 for rotating the chart plate 32 of the sight fixation/subjective measuring system 3 and drives the pulse motor 322. The driver circuit 320 feeds a pulse to a pulse motor 323 for rotating a VCC 37 and drives the pulse motor 323.

Further, the arithmetic/control circuit 301 is connected with the driver circuits 314 through 317 and 325 through 327. The driver circuit 314 is connected to the annular light source 102 of the cornea measuring system 1 and carries out an electric power feed to the annular light source 102 by an electric source circuit (not shown) according to a command from the arithmetic/control circuit 301. The driver circuit 315 feeds an electric power to the light emitting diode 200 of the refractive power measuring system 2 according to a command from the arithmetic/control circuit 301. The driver circuits 314 and 315 are designed as such that they are simultaneously actuated according to a command from the arithmetic/control circuit 301, that is, the light source 102 and the light emitting diode 102 are simultaneously put on or put off.

The driver circuit 316 is connected to the anterior portion illuminating light source 40 of the anterior portion observing/alignment system 4, the driver circuit 317 to the alignment light source 41, the driver circuit 325 to the reticule scale light source 42, and the driver circuit 327 to the glare light source 33, respectively. The work for feeding an electric power to these circuits is also performed according to a command from the arithmetic/control circuit 301. The driver circuits 316, 317 and 318 are actuated by a common command from the arithmetic/control circuit 301, and the light sources 40, 41 and 42 are simultaneously put on or put off. The driver circuit 326 is connected to the light source 30 of the sight fixation/subjective measuring system 3 to feed an electric power thereto according to a command from the control circuit 301.

Furthermore, the arithmetic/control circuit 301 is connected with a second memory 310 for memorizing an axisal angle of each strong/weak main meridian and each radius of curvature measured by the arithmetic/control circuit 301 and also with a third memory 311 for memorizing a spherical power, a cylindrical power and an axial angle value based on the memorized refractive power. The measurement of the spherical power, cylindrical power and axial angle value based on the axial angle value of each strong/weak main meridian, each radius of curvature and refractive power will be described hereinafter in detail.

Figure 11:
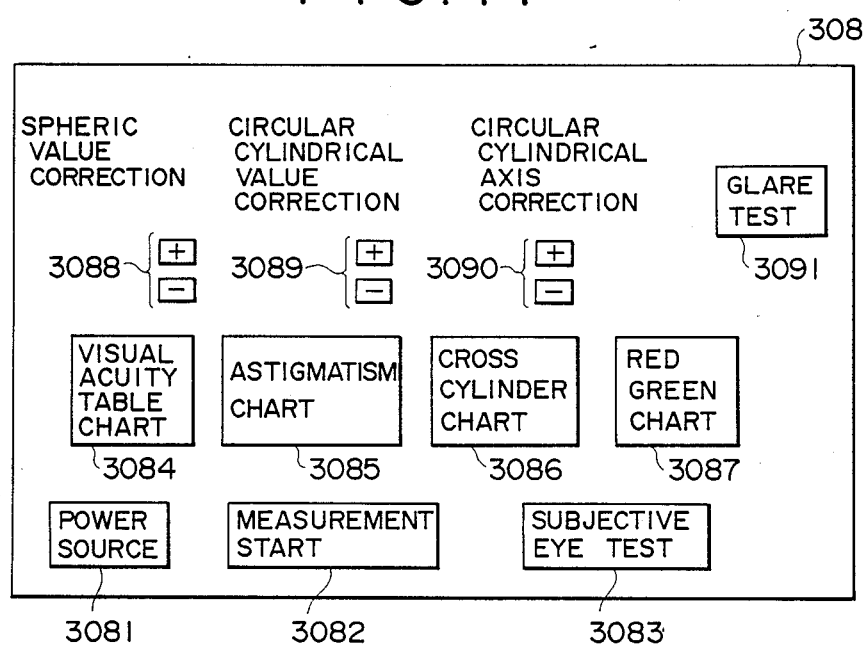
FIG. 11 is a schematic view showing an arrangement of a control switch.

Furthermore, the arithmetic/control circuit 302 is connected with a program memory 307 memorizing a program for calculation and control, and a control switch 308 having various kinds of switches for starting a measurement, selecting a chart for a subjective measurement, for example, as shown in FIG. 11.

A character circuit 306 for converting the measured data memorized in the memories 310 and 311 into a charcater and a numerical figure and outputs them on the display interface 304, is also connected to the arithmetic/control circuit 301.

III. Measuring Steps and Operation

(1) Alignment

Examiner puts on the power switch 3081 of the control switch 308. Then, the driver circuits 316, 317, 325 and 326 are actuated by the arithmetic/control circuit 301, and the light sources 40, 41, 42 and 30 are simultaneously put on. At the same time, the driving circuit 313 is actuated by the arithmetic/control circuit 301. By this, the image receiving element 5 is scanned. At that time, the arithmetic/control circuit 301 switches the gate circuit 302 so that an analog signal from the image receiving element 5 is fed to the display interface 304. By this, the anterior portion of the eye E is illuminated by the light e coming from the light source 40, and the alignment light f coming from the alignment light source 41 is reflected by the anterior portion. Both the light e and f are passed through the measuring optical system 11 of the cornea measuring system 1 and imaged on the image receiving element 5 as an anterior portion image and also as an image of the light source 41 as an alignment target mark, respectively.

Figure 9A:
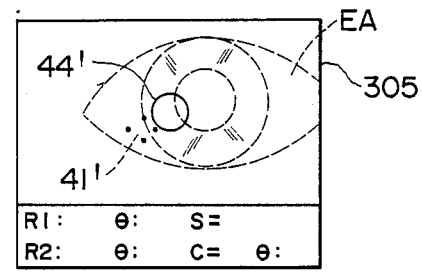
FIGS. 9(a) and 9(b) schematic views showing a displaying device, on which an image is displayed.
Figure 9B:
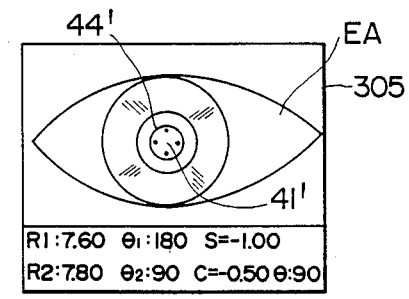

On the other hand, an image of the reticule scale 44 is formed on the image receiving element 5 by the reticule scale light d coming from the light source 42. These three images are converted into analog signals by the image receiving element 5 and output. The analog signals are input into the displaying device 305 through the display interface 304. By this, the displaying device 309, as shown in FIGS. 9(a) and 9(b), displays them as an anterior portion image EA, a reticule scale image 44', and an alignment target dark image 41' thereon. Instead of the light source 41, there may be provided a spot projecting optical system, in which a spot projecting image is reflected by the top of the cornea, so that the spot projecting image is formed on the light receiving element 5 and the alignment is verified based on whether or not the spot projecting image is within a predetermined range on the image receiving element 5.

A person to be tested visually recognizes the sight fixture chart 32a illuminated by the light source 30 through the sight fixation/subjective measuring system 3 which is used partly common with the refractive power measuring system 2. By this, the sight axis of the eye E of the person to be tested is fixed.

The examiner, when the alignment target mark image 41' is presented outside the reticule scale image 44' as shown in FIG. 9(a), moves the whole optical system of the apparatus vertically and horizontally so as to bring the alignment target mark image 41' (see FIG. 9(b)) into the reticule scale image 44' and align the optical axis of the eye E and the optical axis of the objective lens 110. Further, in order to make the anterior portion image EA clear, the whole optical system of the apparatus is moved forward and backward to regulate the working distance to be regular.

(2) Rough Measurement of Refractive Power

Upon completion of the alignment, the examiner puts the measurement starting switch 3082 of the control switch 308 on. According to that command, the arithmetic/control circuit 301 stops a command to the driver circuits 316, 317 and 325 and puts off the light sources 40, 41 and 42 for a short time. However, an issuance of a command to the driver circuit 326 is continued and therefore, the light source 30 is continuously lighted up. The arithmetic/control circuit 301 issues an operating command to the driver circuits 314 and 315 during the existinguishing period of the light sources 40, 41 and 42. Thereafter, until a measurement of the radius of curvature and objective refractive power is finished, the lightening of the light sources 40, 41 and 42, and the lightening of the light sources 102 and 200 are performed in turn. Since the anterior portion observing image is not displayed during the lightening period of the light sources 102 and 200, an indication of, for example, "measurement undergoing" may be displayed on the displaying device 305 at that time. Otherwise, the frame memory 324 may be provided with a memory area for memorizing the anterior portion image so that the anterior portion image memorized in this memory area is displayed on the displaying device 305 during the lightening period of the light sources 102 and 200, i.e., during the measurement.

The cornea measuring light a is passed through the annular opening 100 as a pattern for cornea measurement by emitting the light source 102 and projected to the cornea C. The virtual image 100' based on the cornea C is imaged within the central cornea measuring area 5a (see FIG. 6) of the image receiving element 5 by the measuring optical system 11 of the cornea measuring system 1. Upon emission of the light source 102, the light emitting diode 200 of the objective refractive power measuring system 2 also emits the refractive power measuring light b, the ring pattern image 200' is projected to the retina $E_R$ of the eye E, and the retina reflecting light of the ring pattern 200' is projected to the refractive power measuring area 5b at the peripheral portion of the image receiving element 5 through the measuring optical system 21.

The arithmetic/control circuit 301 switches the gate circuit 302, and the analog signal coming from the image receiving element 5 is input into the A/D converter 303. Thereafter, the arithmetic/control circuit 301 actuates the driving circuit 313, the image receiving element 5 is scanned, and the picture output, i.e., the picture output of the pattern image 100 for measuring the cornea and the picture output of the pattern 203″ for measuring the refractive power, is output to the A/D converter 303. The A/D converter 303 convert the analog signal from the image receiving element 5 to a digital signal, the digital signal is output to the frame memory 324 through the arithmetic/control circuit 301, and information for one screen portion is memorized in the frame memory 324.

Figure 7:
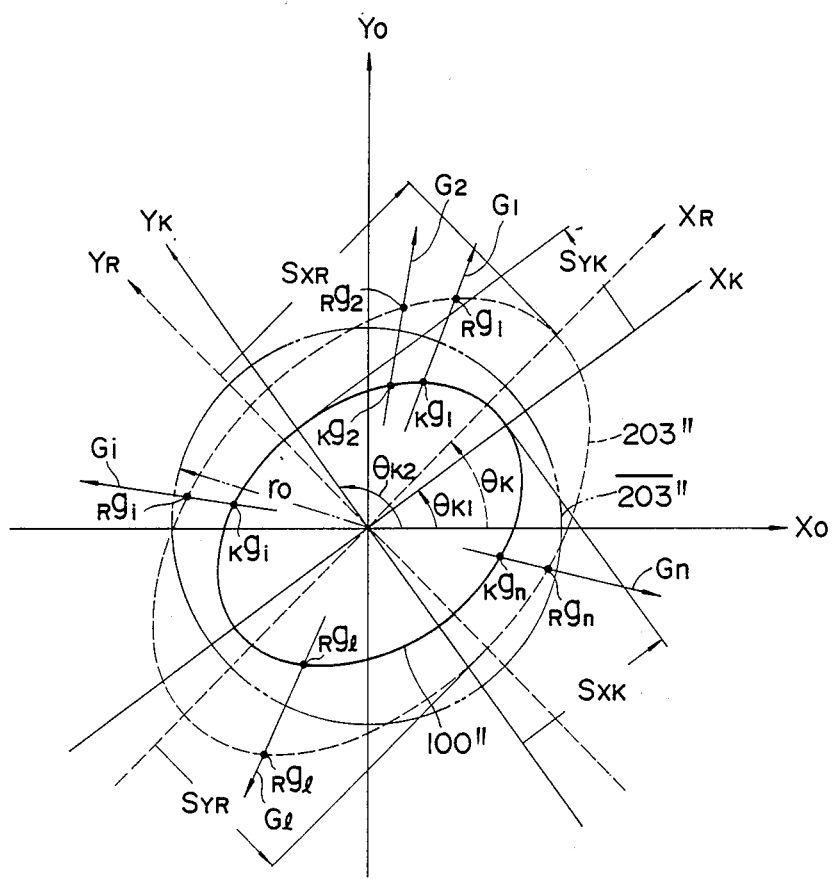
FIG. 7 is a schematic view for explaining a principle for measuring the radius of curvature of a cornea and the refractive power of an eye to be tested from a pattern system.
Figure 6:
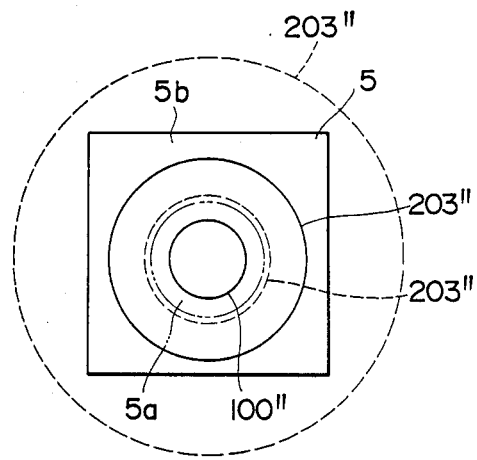
FIG. 6 is a schematic view showing a relation between a light receiving element and a pattern image.

The arithmetic/control circuit 301, as shown in FIG. 7, radially scans and reads the memory address of the frame memory 324 according to a predetermined read scanning $G_1, G_2, \ldots G_i, \ldots G_l, \ldots G_n$. By this, the data corresponding to two images of the pattern image 100″ for measuring the cornea and the pattern 203″ for measuring the refractive power simultaneously projected and imaged onto the image receiving element 5, is scanned and read. If the eye E is suffered from a severe hyperopia, since the pattern image 203″ for measuring the refractive power is projected outside the image receiving element 5 as shown in FIG. 6, only the coordinates $kg_1, kg_2, \ldots kg_i, \ldots kg_l, \ldots kg_n$ on the pattern 100″ for measuring the cornea are read by the above-mentioned scanning.

Similarly, if the eye E is suffered from a severe myopia, the pattern image 100″ for measuring the cornea and the pattern image 203″ for measuring the refractive power are approached.

If the eye E are suffered from both severe hyperopia and myopia, the arithmetic/control circuit 301 outputs a command signal to the driver circuit 318. By this, the arithmetic/control circuit 301 feeds a pulse from the pulse generator 312 to the pulse motor 321 through the driver circuit 318, and causes the movable casing 219 to move so that the pattern image 203″ for measuring the refractive power is projected within the area 5b and the pattern image 203″ for measuring the refractive power and the pattern image 100 for measuring the cornea maintain more than a predetermined distance. Due to the movement of the movable casing 219, the focussing lens 216 is moved. However, the sight fixation chart 32a observed by the eye E through the sight fixation/subjective measuring system 3 is brought to be in a foggy sight state of +1.0 to 2.0 with respect to the refractive power of the eye E.

The number of pulse fed to the pulse motor 321 in order to move the movable casing 219, is counted by the counting circuit in the arithmetic/control circuit 301. The counted value is memorized in the first memory 309 as a moving quantity of the movable casing 219.

(3) Measurement of Radius of Curvature of Cornea & Precision of Objective Refractive Power The control circuit 301 carries out a read scanning $G_1, G_2, \ldots G_i, \ldots G_l, \ldots G_n$, as shown in FIG. 7, based on a final image receiving picture by the image receiving element 5 after the movable casing 29 is moved based on the above-mentioned rough measurement and obtains a coordinate of points $kg_1, kg_2, \ldots kg_i, \ldots kg_l, \ldots kg_n$ on the pattern 100″ for measuring the cornea. Similarly, the coordinate of points $Rg_1, Rg_2, \ldots Rg_i, \ldots Rg_l, \ldots Rg_n$ on the pattern image 203″ for measuring the refractive power is obtained.

(3-1) Measurement of Radius of Curvature of Cornea

The arithmetic/control circuit 301 calculates an ellipse shape of the pattern 100″ from the coordinate of the obtained points $kg_1, kg_2, \ldots kg_i, \ldots kg_l, \ldots kg_n$. The radius $S_{xk}$ of the long axis ($X_k$ axis) correlates to the radius $R_1$ of curvature of a weak main meridian of the cornea C, whereas the radius $S_{yk}$ of the short axis ($Y_k$ axis) correlates to the radius $R_2$ of curvature of the weak main meridian, and the angle $\theta_{k1}$ of the long axis and the angle $\theta_{k2}$ of the short axis correspond to the axial angle $\theta_1$ of the strong main meridian and the axial angle $\theta_2$ of the weak main meridian.

A general formula of the ellipse 100″ in the $X_k$-$Y_k$ coordinate system is expressed as follows:

$$Ax^2 + By^2 + Cxy = 1 \tag{1}$$

$$\begin{aligned} A &= \frac{\cos^2 \theta_{k1}}{(2S_{xk})^2} + \frac{\sin^2 \theta_1}{(2S_{yk})^2} \\ B &= \frac{\sin^2 \theta_{k1}}{(2S_{xk})^2} + \frac{\cos^2 \theta}{(2S_{yk})^2} \\ C &= \frac{2\sin \theta_{k1} \cos \theta_{k1}}{(2S_{xk})^2} - \frac{2\sin \theta_{k1} \cos \theta_{k1}}{(2S_{yk})^2} \end{aligned} \tag{2}$$

Figure 8:
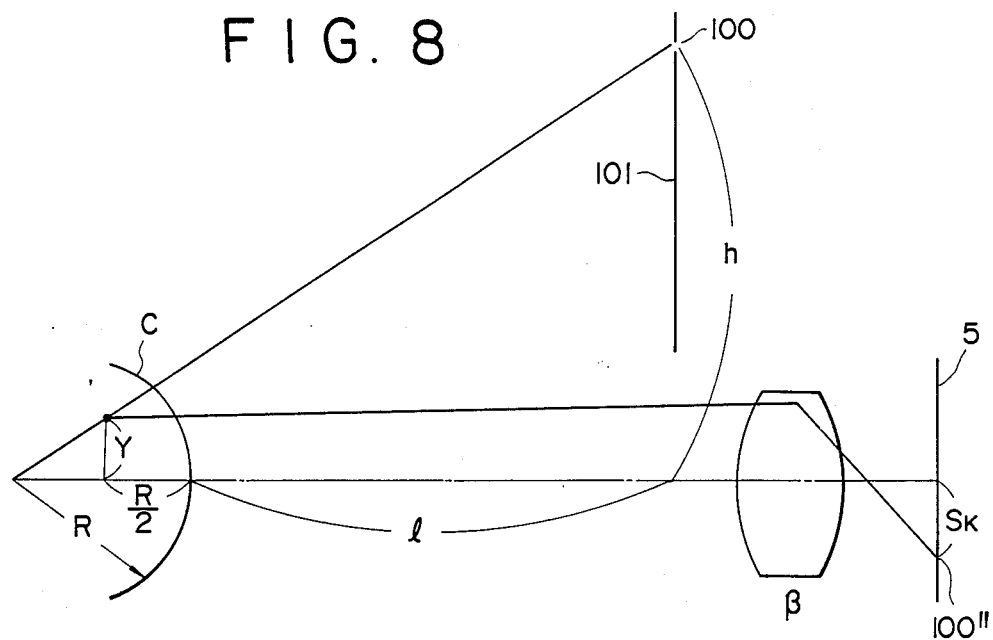
FIG. 8 is a schematic view for explaining a principle for measuring the radius of curvature.

Similarly, the radius $S_k$ of the pattern 100″, as shown in FIG. 8, has the following relation;

$$\begin{aligned} S_k &= Yx \\ Y &= h \times r/2 \end{aligned} \tag{3}$$

wherein R is a radius of curvature of the cornea C, h is the height up to the annular opening 100, l is a working distance, and $\beta$ is a power of the whole projecting optical system. Therefore, in the case of FIG. 7, $S_{xk}$ and $S_{yk}$ are obtained from the (1) and (2) formulas, and the radius $R_1$ of curvature of the strong main meridian can be obtained from the (3) formula as follows;

$$R_1 = \frac{2 S_{yR} \cdot l}{\beta \cdot h} \tag{4}$$

and similarly, the radius $R_2$ of curvature of the weak main meridian can be obtained as follows;

$$R_2 = \frac{2 S_{xk} \cdot l}{\beta \cdot h} \tag{4'}$$

Also, the axial angle $\theta_1 = \theta_{k2}$ of the strong main meridian and the axial angle $\theta_2 = \theta_{k1}$ of the weak main meridian can be obtained. Such obtained the radii $R_1$ and $R_2$ of curvature and the axial angles $\theta_1$ and $\theta_2$ are displayed on the displaying device 305 together with the anterior portion through the character circuit 306 and display interface 304 as shown in FIG. 9(b) and memorized by the second memory 310.

(3-2) OBJECTIVE REFRACTIVE POWER MEASUREMENT

Based on the coordinate of the points $R_{g1}, R_{g2}, \ldots R_{gi}, \ldots R_{gl}, \ldots R_{Rgn}$ of the pattern image 203'' for measuring the refractive power obtained by the read scanning, like the above-mentioned (1) formula and (2) formula, the general formula of the ellipse 203'' in the $X_R$-$Y_R$ coordinate is as follows;

$$Ax^2 + By^2 + Cxy = 1 \quad (1)$$

$$\begin{aligned} A &= \frac{\cos^2 \theta_R}{(2S_{xR})^2} + \frac{\sin^2 \theta_R}{(2S_{yR})^2} \\ B &= \frac{\sin^2 \theta_R}{(2S_{xR})^2} + \frac{\cos^2 \theta_R}{(2S_{yR})^2} \\ C &= \frac{2\sin\theta_R \cdot \cos\theta_R}{(2S_{xR})^2} - \frac{2\sin\theta_R \cdot \cos\theta_R}{(2S_{yR})^2} \end{aligned} \quad (2)'$$

From these formulas (1) and (2), $S_{xR}$ and $S_{yR}$ are obtained. Then, the refractive power $D_1$ of the strong main meridian and the refractive power $D_2$ of the weak main meridian, in the example of FIG. 7, is obtained as follows;

$$\begin{aligned} D_1 &= D_{yR} = (S_{yR} - r_0)\frac{1}{fx} \text{ (unit of } f \text{ and } x \text{: } m) \\ D_2 &= D_{xR} = (S_{xR} - r_0)\frac{1}{fx} \text{ (unit of } f \text{ and } x \text{: } m) \end{aligned} \quad (5)$$

wherein $r_0$ is the radius of the pattern image 203'' of the 0 diopter, f is a composing focal distance of the measuring optical system 21, and x is basic line length (i.e., the radius of a conjugated image of the ring diaphragm at the position of the pupil of the eye E).

Next, the arithmetic/control circuit 301 reads the moving amount, i.e, the number of pulse corresponding to the moving amount of the focussing lens 216, of the movable casing 219 memorized in the first memory 309, and from this pulse number, $(D_1+d)$, $(D_2+d)$ are obtained by adding the refractive power correcting portion d due to movement of the focussing lens 216 to the refractive powers $D_1$ and $D_2$ of the strong/weak meridians obtained by the (5) formula. By this, a spheric refractive power S, a cylindrical refractive power C and a cylindrical axial angle $\theta$ is obtained as follows:

$$\begin{aligned} S &= (D_2 + d) \\ C &= (D_1 + d) - (D_2 + d) \\ \theta &= \theta_k \end{aligned} \quad (6)$$

The arithmetic/control circuit 301 displays such obtained S, C and $\theta$ on the displaying device 305 through the display interface 304 and causes the third memory 311 to memorize them.

(4) Subjective Refractive Power Measurement

When the examiner puts on the subjective eye testing switch 3083 of the control switch 308 next, the arithmetic/control circuit 301 stops the issuance of a command to the drivers 314 and 315, and thereafter, the light sources 102 and 200 stops the emission of light. When the examiner selects the visual acuity test chart by the chart selecting switch 3089 of the control switch 308 next, the arithmetic/control circuit 301 actuates the driver circuit 319. By this, a predetermined number of pulse is fed to the pulse motor 322 from the pulse generator 312. As a result, the chart plate 32 is rotated, and the visual acuity table chart 32b (see FIG. 10) is inserted into the optical path of the subjective measuring system 3.

The arithmetic/control circuit 301 reads the refractive characteristics S, C and $\theta$ of the eye E obtained by the objective refractive power measurement and memorized in the second memory 311 and calculates the pulse number required for moving the focussing lens 216 based on the value of the spheric refractive power S. Such obtained number of pulse is fed to the pulse motor 321 through the driver circuit 318. As a result, the movable casing 219 is moved, and the focussing lens 216 is moved.

Next, the arithmetic/control circuit 301 calculates the pulse number for rotating the VCC 37 from the cylindrical refractive power and the axial angle $\theta$, and such obtained number of pulse is fed to the pulse motor 323 through the driver circuit 320. As a result, the VCC 37 is rotated. By this, the subjective measuring system 3 is optically corrected corresponding to the refractive power of the E obtained by the objective refractive power measurement.

The person to be tested sees the visual acuity chart 32b inserted into the subjective measuring system 3 and answers the direction where the Randolt ring is partly cut. The examiner determines the subjective visual acuity of the eye E from the answer of the person to be tested. If the examiner determines that the corrected visual acuity is not sufficient yet, he operates a spheric power correcting switch 3088 of the control switch 318. The arithmetic/control circuit 301 feeds the pulse from the pulse generator 312 to the pulse motor 321 through the driver circuit 318 to move the focussing lens to a position, again, where the corrected visual acuity is improved. The arithmetic/control circuit 301 counts the pulse number at the time when the focussing lens is moved again, then obtains the d of the formula (6) from this pulse number, then calculates the S, C and $\theta$ from the formula (6) based on this newly obtained d, and then displays the value on the displaying device 305.

When the examiner selects an astigmatism chart switch 3085 of the control switch 308 next, a predetermined number of pulse is fed to the pulse motor 322 through the driver circuit 319. By this, the chart plate 32 is rotated, and the astigmatism chart switch 32c is inserted into the optical path of the subjective measuring system 3. The person E to be tested sees the astigmatism chart switch 32c inserted and answers whether or not a thick line is present. When the person to be tested answers "yes", the examiner operates the cylindrical axis correcting switch 3090 of the control switch 308.

According to that command, the arithmetic/control circuit 301 feeds pulse to the pulse motor 323 through the driver circuit 320 and rotates the VCC 37 to correct the cylindrical axis. The arithmetic/control circuit 301 counts the pulse number. The angle θ of the cylindrical axis is corrected based on the counted value, and the angle of the cylindrical axis after the correction is displayed on the displaying device 305.

Next, the examiner selects a cross cylinder chart switch 3086 of the arithmetic/control switch 308. By this, the control circuit 301 controls the pulse motor 323 to make, alternately, a difference of ±0.5 D, for example, in the angle of the cylindrical axis with reference to the cylindrical power C currently set. The examiner asks the person to be tested about the difference of view of the chart 32d at that time. And, if the person to be tested thinks that there is a difference in view, he operates the cylindrical power correcting switch 3089 of the control switch 308. By this, the arithmetic/control circuit 301 controls the VCC 37 according to that command. As a result, the cylindrical power is corrected, and a new cylindrical power is displayed on the displaying device 305.

Next, the examiner selects a red green chart switch 3087 of the control switch 308. By this, the arithmetic/control circuit 301 actuates the pulse motor 322, and the red green chart 32e is inserted into the subjective measuring system 3. The person to be tested answers how the red green chart 32e looks. The examiner controls the spheric power correcting switch 3088 of the control switch 308 depending on the answer of the person to be tested. Upon receipt of a command, the arithmetic/control circuit 301 actuates the pulse motor 321. By this, the focussing lens 216 is moved, the spheric power S is corrected, and a new spheric power is displayed on the displaying device 305.

(5) Glare Test

The examiner selects a glare test switch 3091 of the control switch 308 next. Then, the arithmetic/control circuit 301 actuates the pulse motor 322 through the driver circuit 319. By this, the chart plate 32 is rotated and the visual acuity chart 32b is inserted into the optical path of the subjective measuring system 3. At the same time, the driver circuit 327 is actuated and the glare light source 33 emits light.

The person to be tested sees the visual acuity chart 32b under the blinding flash of the light emitted by the glare light source. The examiner can determine whether or not the eye E is slightly suffered from a cataract, from his answer. The glare light source may be provided with a known volume, etc. so that the brightness can be varied.

As described in the foregoing, according to the present invention, two pattern images can be scanned by one scanning in order to project, simultaneously, a cornea measuring pattern from the cornea for measuring the corneal configuration and a refractive power measuring pattern from the eye pressure for measuring the eye refractive power, to different areas of one image receiving element. Accordingly, since the circuit for driving the image receiving element and the arithmetic processing system can be commonly used, the eye testing apparatus can be made small. In addition, the counting time can be shortened.

While specific embodiments of the present invention have been shown and described in detail to illustrate the application of the principles of the present invention, it will be understood that the present invention may be embodied otherwise without departing from such principles.

What is claimed is:

1. An eye testing apparatus, in which a corneal reflecting image and a retinal reflecting image formed by projecting a target mark image onto a cornea and a retina of an eye to be tested are projected to a light receiving portion through a measuring optical system, and in which a corneal configuration and a refractive power of the eye to be tested are measured according to a signal detected by the light receiving portion comprising:

a two-dimensional light receiving element in said light receiving portion, and wherein said measuring optical system includes a means for simultaneously projecting said corneal reflecting image and said retinal reflecting image in separate optical paths to different areas of said two-dimensional light receiving element for simultaneously reception.

2. The eye testing apparatus as claimed in claim 1, wherein said two-dimensional light receiving element comprises an area CCD.

3. The eye testing apparatus as claimed in claim 1, wherein said corneal reflecting image is formed at a central area of said two-dimensional light receiving element, and said retinal reflecting image is formed at a peripheral area of said two-dimensional light receiving element.

4. An eye testing apparatus comprising:

first pattern projecting means for projecting a first annular pattern image to the corneal of the eye to be tested for measuring a radius of curvature of the cornea;

second pattern projecting means for projecting a second annular pattern image to the retina of the eye to be tested for measuring the refractive power of the eye;

measuring optical means including a two-dimensional light receiving element for simultaneously projecting a corneal reflecting image of the first annular pattern image for measuring the radius of curvature of the cornea of the eye and a retinal reflecting image of the second annular pattern image for measuring the refractive power of the eye, to different areas of said two-dimensional light receiving element for simultaneously reception.

5. The eye testing apparatus as claimed in claim 4, wherein said two-dimensional light receiving element comprises an area CCD.

6. The eye testing apparatus as claimed in claim 4, wherein said corneal reflecting image is formed at a central area of said two-dimensional light receiving element, and said retinal reflecting image is formed at a peripheral area of said two-dimensional light receiving light element.

7. An eye testing apparatus comprising:

first pattern projecting means for projecting a first annular pattern image toward the cornea of an eye to be tested for measuring a radius of curvature of the cornea;

second pattern projecting means for projecting a second annular pattern image toward the retina of an eye to be tested for measuring the refractive power of the eye;

measuring optical means including a two-dimensional light receiving element for simultaneously projecting a corneal reflecting image based on the first annular pattern image for measuring the radius of curvature of the cornea of the eye and a retinal image based on the second annular pattern image for measuring the refractive power of the eye, to different areas of said two-dimensional element for simultaneous reception; and electric circuit means for scanning said two-dimensional light receiving element and obtaining a detecting signal corresponding to the corneal reflecting image and a detecting signal corresponding to the retinal reflecting image to obtain simultaneously a corneal configuration and a refractive power of the eye.

8. The eye testing apparatus as claimed in claim 7, wherein said two-dimensional light receiving element comprises an area CCD. in 9. The eye testing apparatus as claimed in claim 7, where said corneal reflecting image is formed at a central area of said two-dimensional light receiving element, and said retinal reflecting image is formed at a peripheral area of said two-dimensional light receiving element.

10. The eye testing apparatus as claimed in claim 7, wherein said second pattern projecting means includes means for moving the second annular pattern image in order to avoid forming the corneal reflecting image and the retinal reflecting image adjacent to each other on said two-dimensional light receiving element due to a severe myopia of the eye.

11. An eye testing apparatus comprising:

first pattern projecting means for projecting a first pattern image toward the cornea of an eye to be tested for measuring a radius of curvature of the cornea;

second pattern projecting means for projecting a second pattern image toward the retina of the eye to be tested for measuring the refractive power of the eye, said first pattern projecting means and said second pattern projecting means comprising two separate optical paths;

measuring optical means including a two-dimensional light receiving element for simultaneously projecting a corneal reflecting image based on the first pattern image and a retinal reflecting image based on the second pattern image to different areas of the two-dimensional light receiving element;

electric circuit means for scanning said two-dimensional light element and obtaining a first detecting signal corresponding to said corneal reflecting image and a second detecting signal corresponding to said retinal reflecting image, to obtain a corneal configuration and the refractive power of the eye;

sight fixation/subjective measuring optical means for projecting a sight fixation mark for fixing the sight of the eye and a test chart for subjective testing the refractive characteristics of the eye; and anterior portion observing/alignment optical means for observing an anterior portion of the eye and aligning an optical axis of the apparatus with the sight axis of the eye.

12. The eye testing apparatus as claimed in claim 11, wherein said two-dimensional light receiving element comprises and area CCD.

13. The eye testing apparatus as claimed in claim 11, wherein said corneal reflecting image is formed at a central area of said two-dimensional light receiving element and said retinal reflecting image is formed at a peripheral area of said two-dimensional light receiving element.

14. The eye testing apparatus as claimed in claim 11, wherein said second pattern projecting means includes means for moving the second pattern image in order to avoid forming the corneal reflecting image and the retinal reflecting image adjacent to each other on said two-dimensional light receiving element due to a severe myopia of the eye.

15. The eye testing apparatus as claimed in claim 11, wherein said anterior portion observing/alignment optical means has an optical path that is partly common with that of said measuring optical means.

16. The eye testing apparatus as claimed in claim 11, wherein a wavelength of light used for forming the first pattern image is different from a wavelength of light used for forming the second pattern image.

17. The eye testing apparatus as claimed is claim 11, wherein said sight fixation/subjective measuring optical means includes a light source for a glare test.

* * * * *

UNITED STATES PATENT AND TRADEMARK OFFICE
CERTIFICATE OF CORRECTION

PATENT NO. : 4,859,051
DATED : August 22, 1989
INVENTOR(S) : YASUFUMI FUKUMA ET AL It is certified that error appears in the above-identified patent and that said Letters Patent is hereby corrected as shown below:

IN THE ABSTRACT

Line 4, change "slight" to --light--.

IN THE CLAIMS

Claim 4, line 3, change "corneal" to --cornea--;
line 18, change "simultaneously" to --simultaneous--.
Claim 6, line 6, delete "light".
Claim 8, line 3, delete "in".

Signed and Sealed this

First Day of January, 1991

Attest:

HARRY F. MANBECK, JR.

Attesting Officer

Commissioner of Patents and Trademarks